United States Patent
Castro

(10) Patent No.: US 6,409,997 B1
(45) Date of Patent: Jun. 25, 2002

(54) WAX COSMETIC STICK

(75) Inventor: Mauricio Castro, Ranchos Palos Verdes, CA (US)

(73) Assignee: Neutrogena Corporation, Los Angeles, CA (US)

( * ) Notice: Subject to any disclaimer, the term of this patent is extended or adjusted under 35 U.S.C. 154(b) by 0 days.

(21) Appl. No.: 09/628,483

(22) Filed: Jul. 31, 2000

(51) Int. Cl.$^7$ .............. A61K 7/42; A61K 7/44; A61K 7/021; A61K 7/025; A01N 25/08

(52) U.S. Cl. .............. 424/59; 424/60; 424/63; 424/64; 424/400; 424/401; 424/409; 424/DIG. 5

(58) Field of Search .............. 424/400, 401, 424/59, 60, 63, 64, DIG. 5, 409

(56) References Cited

U.S. PATENT DOCUMENTS

| | | | |
|---|---|---|---|
| 4,127,672 A | | 11/1978 | Klier et al. |
| 4,756,905 A | | 7/1988 | Melnik |
| 4,919,934 A | * | 4/1990 | Deckner et al. ............ 424/401 |
| 5,465,685 A | | 11/1995 | Dotolo et al. |
| 5,489,433 A | | 2/1996 | Aboud |
| 5,565,208 A | | 10/1996 | Vlasblom |
| 5,672,337 A | | 9/1997 | Ascione et al. |
| 5,716,602 A | | 2/1998 | Uick |
| 5,744,146 A | * | 4/1998 | Peters et al. ................ 424/401 |
| 5,843,407 A | * | 12/1998 | El-Nokaly et al. ............ 424/64 |
| 5,961,997 A | * | 10/1999 | Swinehart .................... 424/401 |
| 6,024,738 A | * | 2/2000 | Stepniewski et al. ........ 424/401 |
| 6,183,766 B1 | * | 2/2001 | Sine et al. .................. 424/405 |

FOREIGN PATENT DOCUMENTS

| | | |
|---|---|---|
| EP | 0 097 812 A1 | 6/1982 |
| EP | 0 097 813 A1 | 1/1984 |
| WO | WO-96/15760 A * | 5/1996 |
| WO | WO-96/15762 A * | 5/1996 |

OTHER PUBLICATIONS

Neutrogena Sunblock Stick SPF 25 product packaging, publishing available prior to Jul. 31, 2000.
SolarSense Face & Lip Protection CCA Industries, Inc. product packaging, publishing available prior to Jul. 31, 2000.
Mustela Sunblock Stick Laboratories Pharmascience product container, publishing available prior to Jul. 31, 2000.
Coppertone Shade Sunblock product packaging, 1997.
The Body Shop Facial Sun Stick Ultra Protection Product packaging, publishing available prior to Jul. 31, 2000.
Clarins Stick Solaire Haute Protection product packaging, publishing available prior to Jul. 31, 2000.
International Cosmetic Ingredient Dictionary and Handbook, Seventh Edition, vol. 2, 1997, The Cosmetic, Toiletry, and Fragrance Association, pp. 1565–1567, 1574–1575, 1613, 1633, 1636, 1656–1661, and 1672.
M.S. Balsam, M.M. Rieger, E. Sagarin, S.D. Gershon, S.J. Strainse, Cosmetics Science and Technology, Second Edition, vol. 1, Chapter VIII, Wiley–Interscience, pp. 189–212, 1957.

* cited by examiner

*Primary Examiner*—Jose G. Dees
*Assistant Examiner*—Marina Lamm
(74) *Attorney, Agent, or Firm*—William E. McGowen

(57) ABSTRACT

The present invention relates to a cosmetic stick composition comprising (a) a skin care agent and (b) a solid wax, wherein the composition comprises less than 1%, by weight, of oil, and methods of using such composition.

25 Claims, No Drawings

WAX COSMETIC STICK

FIELD OF THE INVENTION

The present invention relates to a solid cosmetic stick composition comprising a skin care agent and a solid wax, wherein said composition comprises less than 5%, by weight, of oil.

BACKGROUND OF THE INVENTION

In the field of cosmetics, three types of solid cosmetic stick formulations exist for the delivery of skin care agents such as sunscreens and antiperspirants: compressed powder sticks, gel sticks, and wax sticks. All of these product forms have their benefits and weaknesses. Compressed powder sticks are dry, but tend to flake off upon application to the skin. Gel sticks tend to be smooth upon application, but remain sticky on the skin. Wax sticks tend to be smooth upon application and less sticky on the skin, but existing wax sticks have a greasy feel and leave a visible shiny, grease film on the skin.

A number of solid cosmetic sticks are currently sold to deliver sunscreens to the skin, e.g., Coppertone Shade® Sunblock Stick SPF 30, Mustela Sunblock Stick SPF 20, Solar Sense® Face & Lip Protection, The Body Shop Facial Sun Stick, Neutrogena® Sunblock Stick SPF 25, and Clarins Paris Stick Solaire Haute Protection. All of these products, however, comprise oils such as castor oils and polybutenes.

The present invention provides a solid cosmetic stick formulation that contains a skin care agent that is substantially free of such oils, thus, both reducing shine and a greasy-feel when applied to the skin.

SUMMARY OF THE INVENTION

In one aspect, the invention features cosmetic stick composition comprising (a) a skin care agent and (b) a solid wax, wherein the composition comprises less than 1%, by weight, of oil. In one embodiment, the skin care agent is selected from the group consisting of sunscreens, insect repellants, analgesics, non-oil emollients, vitamins, and deodorants. In one embodiment, the composition further comprises a non-oil emollient and/or a mattifier. In one embodiment, the composition is anhydrous and/or comprises less than 0.5% such as 0%, by weight, of oil.

The present invention also features methods of using the above compositions (e.g., methods of administering a skin care agent such as a sunscreen).

Other features and advantages of the present invention will be apparent from the detailed description of the invention and from the claims.

DETAILED DESCRIPTION OF THE INVENTION

It is believed that one skilled in the art can, based upon the description herein, utilize the present invention to its fullest extent. The following specific embodiments are to be construed as merely illustrative and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference.

The present invention relates to a cosmetic stick composition comprising a skin care agent and a solid wax. What is meant by the term "oil" is an animal (e.g., fatty acid esters), mineral (e.g., paraffinic oils), vegetable (e.g., vegetable oils), or synthethic hydrocarbons that are liquid at room temperature, soluble in organic solvents, and substantially not soluble in water (e.g., less than 0.1 mg/ml at 250). Examples of oils include but are not limited to: mineral oils such as paraffinic oils; synthetic hydrocarbons such as polybutene and polyisobutene; vegetable oils such as castor oils, sesame oils, and peanut oils; and animal oils and fats such as triglycerides and butters. Other examples of fats, oils, and hydrocarbons are found in the International Cosmetic Ingredient Dictionary and Handbook, eds. Wenninger and McEwen, pp. 1565–67 and 1574–75 (The Cosmetic, Toiletry, and Fragrance Assoc., Washington, D.C., $7^{th}$ Ed., 1997) (hereinafter "ICI Handbook"). In one embodiment, the compositions of the present invention comprises less than 1%, by weight, of oil or does not comprise any oil.

Waxes are similar to oils, except that unlike oils, waxes are not liquid at room temperature. Waxes include animal waxes, plant waxes, mineral waxes, and petroleum waxes. Examples of waxes include, but are not limited to, beeswax, paraffin wax, ozokerite, candelilla wax, cetyl alcohol, stearyl alcohol, spermaceti, carnauba wax, baysberry wax, montan, ceresin, and microcrystalline waxes. Other examples of waxes are found on pages 1604–05 of the ICI Handbook. In one embodiment, the composition comprises a total amount of about 10% to about 90%, by weight, of wax, e.g., from about 20% to about 90%, by weight, of wax.

What is meant by a "skin care agent" is any ingredient that offers a cosmetic, pharmaceutical, or therapeutic benefit when applied to the skin of a mammal (e.g., when topically administering to the skin of a human). Examples of a skin care agent include, but are not limited to, sunscreens, anti-acne agents (e.g., benzoyl peroxide and salicylic acid), analgesics, emollients, vitamins, self-tanning agents (e.g., dihydroxyacetone), deodorants, and anti-perspirants.

Sunscreens are compounds that absorb radiation in the UV range of wavelengths. Examples of sunscreens useful herein include, but are not limited to, aminobenzoic acid, homosalate, octocrylene, avobenzone, octyl salicylate, octyl methoxycinnamate, titanium dioxide, zinc oxide, oxybenzone, padimate O, trolamine salicylate, dioxybenzone, and menthyl anthranilate. Other sunscreens useful herein can be found in Sagarin, Cosmetics Science and Technology, Chapter VIII, pages 189 et seq. and the ICI Handbook page 1672. A list of sunscreens is also disclosed in U.S. Pat. No. 4,919,934. The sunscreen concentration can range from about 1% to about 30%, by weight, of the composition (e.g., from about 2% to about 20%). The total concentration should be based on the desired SPF level (e.g., an SPF level of from about 10 to about 50).

Insect repellents may also be delivered by the compositions of the present invention. Examples of insect repellents include, but are not limited to, citronella oil, N,N-diethyltoluamide (DEET), ethyl 3-(N-butylacetamido) propionate, and natural or synthetic pyrethoids. Example of insect repellents are disclosed in European patent applications 097,812 and 097,813 and U.S. Pat. Nos. 4,127,672, 4,756,905, 5,465,685, 5,489,433, 5,565,208, 5,672,337 and 5,716,602. The amount of insect repellent depends on the activity of the compound and can range from about 0.01% to about 10%, by weight, of the composition.

Analgesics are compounds that have a topical analgesic, anesthetic, or antipruritic effect by depressing cutaneous sensory receptors, or that have a topical counterirritant effect by stimulating cutaneous sensory receptors. Examples of analgesics useful herein include, but are not limited to, camphor, capsaicin, and menthol. A list can also be found in the ICI Handbook on page 1636. The amount of an analgesic in the composition can range from about 0.1% to about 40% (e.g., about 0.1% to about 10%), by weight of the composition.

Non-oil emollients are compounds, that are not oils, that help to maintain the soft, smooth, and pliable appearance of the skin as a result of their ability to remain on the skin surface or in the stratum cornuem to act as lubricants to reduce flaking, and improve the skin appearance. Examples of non-oil emollients include, but are not limited to, C12–15 alkyl benzoate, neopentyl glycol dioctanoate, neopentyl glycol diisostearate, butyl octyl salicylate, and dibutyl adipate. Other non-oil emollients can be found on pages 1656–1661 of the ICI Handbook.

What is meant by a vitamin is an organic substance occurring in foods and necessary in trace amounts for the normal metabolic functioning of the body. Examples of such vitamins include, but are not limited to, vitamin A (retinol), a vitamin B (e.g., vitamin B1, vitamin B2, vitamin B6, or vitamin B12), vitamin C, and a vitamin E (e.g., a tocopherol or a tocotrienol), and a therapeutically acceptable hydrate, salt, or ester thereof, such a retinyl palmitate, retinyl acetate, and tocopherol acetate, ascorbyl palmitate, toctrienol, tocotrienyl acetate, tocopherol, tocopheryl acetate, cholecalciferol, menaquinone, and phylloquinone. The amount of vitamin in the composition can range from about 0.01% to about 10%, by weight of the composition.

Deodorants are compounds that reduce or eliminate unpleasant odor and protect against the formation of malodor on body surfaces. Anti-perspirants are products that reduce the production of perspiration or sweat at the location they are applied. Examples include, but are not limited to, aluminum chloride, aluminum chlorohydrate, aluminum dichlorohydrate, aluminum sulfate, and aluminum zirconium octachlorohydrate. More examples of deodorant agents and anti-perspirants can be found in the ICI Handbook page 1633 and page 1613.

What is meant by a mattifying agent is a compound that reduces the shine of skin at the location they are applied. Examples of mattifying agent include, but are not limited to, silica, a silicone elastomer such as divinylmethicone, vinyldimethicone cross polymer, and polysilicone-11, nylons, and starches.

One with ordinary skill in the art can also add other ingredients to the composition such as fragrances, colorants, preservatives, conditioning agents, and waterproofing agents.

The compositions of the present invention may be stored in containers suitable for delivering such compositions, e.g., those compositions currently used to administer lipsticks, lipbalms, insect repellent and sunscreen sticks. Examples of such containers can be purchased from Federal Package Network, Inc. (Chaska, Minn.) and Cosmopack (New York, N.Y.).

The compositions may be applied to the skin (e.g., the face), lips, hair, or nails of the user to deliver the skin care agent as often and in such quantities as necessary to obtain the benefit of the skin care agent (e.g., the sunscreen or insect repellent).

The composition and formulations containing such compositions of the present invention may be prepared using methodology that is well known by an artisan of ordinary skill. The following is a description of the manufacture of a composition of the present invention. Other compositions of the present invention can be prepared in an analogous manner by a person of ordinary skill in the art.

EXAMPLE 1

Sunscreen Cosmetic Stick

A cosmetic stick comprising a sunscreen and waxes and not comprising any oils having the following ingredients listed in Table I was manufactured as follows:

TABLE I

| INGREDIENT | WEIGHT % |
|---|---|
| Homosalate | 15 |
| Cyclopentasilicone/polysilicone-11/dimethicone | 10 |
| Paraffin wax | 10 |
| $C_{12-15}$ alkyl benzoate | 8.63 |
| Ozokerite | 8 |
| Octyl methoxycinnamate | 7.5 |
| Candelilla wax | 6 |
| Octyl salicylate | 5 |
| Neopentyl glycol dioctanoate/diisostearate | 5 |
| Butyloctyl salicylate | 5 |
| Dibutyl adipate | 5 |
| Beeswax | 5 |
| Polyethylene | 4 |
| Cetyl alcohol | 3 |
| Avobenzone | 2 |
| Fragrance | 0.5 |
| Propyl paraben | 0.1 |
| Tocopheryl acetate | 0.1 |
| Ascorbyl palmitate | 0.1 |
| Retinyl palmitate | 0.05 |
| Butylated hydroxy toluene | 0.02 |

The cosmetic stick was made using the following procedure. The $C_{12-15}$ alkyl benzoate (Finsolv TN from Finetex, Elmwood Park, N.J.), homosalate, octyl methoxycinnamate, octyl salicylate, neopentyl glycol dioctyl/diisostearate (Minno-21 from Bernel Chemical Company, Englewood, N.J.), butyloctyl salicylate (Hallbrite BHB from C. P. Hall Co., Chicago, Ill.), and dibutyl adipate (Cetiol-B from Cognis, Ambler, Pa.) were added into a beaker. The composition was mixed thoroughly until homogeneous. Then, avobenzeone (Parsol 1789 from Roche Specialty and Cosmetic Group, Parsippany, N.J.) was added to the mixture. The composition was then heated until a clear solution was achieved. The following ingredients were then added: polyethylene 400 (New Phase Technology, Piscataway, New Jersey), beeswax, paraffin wax, ozokerite, cetyl alcohol, candelilla wax, propyl paraben, tocopheryl acetate, butylated hydroxytoluene, and ascorbyl palmitate. This mixture was heated to about 85° C. Once a clear solution was achieved, the silicone elaster/cyclomethicone was added (Gransil DMCM-5 from Grant Industries, Elmwood Park. N.J.). Upon homogenity, the mixture was allowed to cool down below 55° C. The fragrance and retinyl palmitate were added, and mixed until homogeneous.

It is understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. A cosmetic stick composition comprising, (a) a skin care agent;

(b) a solid wax;

(c) a non-oil emollient selected from the group consisting of C12–15 alkyl benzoate, neopentyl glycol dioctanoate, neopentyl glycol diisostearate, butyloctyl salicylate, and dibutyl adipate; and (d) a silicone elastomer, wherein said composition comprises less than 1%, by weight, of oil.

2. A composition of claim 1, wherein said composition comprises a total amount of about 10% to about 90%, by weight, of wax.

3. A composition of claim 2, wherein said solid wax is selected from the group consisting of beeswax, paraffin wax, ozokerite, candelilla wax, cetyl alcohol, stearyl alcohol, spermaceti, carnauba wax, baysberry wax, montan, ceresin, and microcrystalline waxes.

4. A composition of claim 1, wherein said composition comprises about 0.01% to about 40%, by weight, of a skin care agent.

5. A composition of claim 3, wherein said composition comprises about 0.01% to about 40%, by weight, of a skin care agent.

6. A composition of claim 1, wherein said skin care agent is a sunscreen.

7. A composition of claim 4, wherein said skin care agent is a sunscreen.

8. A composition of claim 5, wherein said skin care agent is a sunscreen.

9. A composition of claim 8, wherein said skin care agent is a sunscreen selected from the group consisting of octyl methoxycinnamate, titanium dioxide, zinc oxide, aminobenzoic acid, octocrylene, methyl anthranilate, avobenzone, octyl salicylate, oxybenzone, and homosalate.

10. A composition of claim 1, wherein said composition is anhydrous.

11. A composition of claim 9, wherein said composition is anhydrous.

12. A composition of claim 1, wherein said composition comprises less than 0.5 percent, by weight, of oil.

13. A composition of claim 11, wherein said composition comprises less than 0.5 percent, by weight, of oil.

14. A method of administering a skin care agent, said method comprising applying a cosmetic stick composition comprising (a) a skin care agent;

(b) a solid wax;

(c) a non-oil emollient selected from the group consisting of C12–15 alkyl benzoate, neopentyl glycol dioctanoate, neopentyl glycol diisostearate, butyloctyl salicylate, and dibutyl adipate; and (d) a silicone elastomer, wherein said composition comprises less than 1%, by weight, of oil.

15. A composition of claim 9, wherein:

said wax is selected from the group consisting of paraffin wax, ozokerite, candelilla wax, beeswax, and cetyl alcohol;

said non-oil emollient is selected from the group consisting of $C_{12-15}$ alkyl benzoate, neopentyl glycol dioctanoate, dibutyl adipate, and butyloctyl salicylate; and said sunscreen is selected from the group consisting of homosalate, octyl methoxycinnamte, octyl salicylate, and avobenzone;

wherein said composition is anhydrous.

16. A composition of claim 15, wherein said silicone elastomer is polysilicone-11.

17. A method of claim 14, wherein said composition comprises a total amount of about 10% to about 90%, by weight, of wax and said solid wax is selected from the group consisting of beeswax, paraffin wax, ozokerite, candelilla wax, cetyl alcohol, stearyl alcohol, spermaceti, camauba wax, baysberry wax, montan, ceresin, and microcrystalline waxes.

18. A method of claim 17, wherein said composition comprises about 0.01% to about 40%, by weight, of a skin care agent and said skin care agent is a sunscreen.

19. A method of claim 18, wherein said skin care agent is a sunscreen selected from the group consisting of octyl methoxycinnamate, titanium dioxide, zinc oxide, aminobenzoic acid, octocrylene, methyl anthranilate, avobenzone, octyl salicylate, oxybenzone, and homosalate.

20. A method of claim 19, wherein said composition is anhydrous.

21. A composition of claim 1, wherein said silicone elastomer is polysilicone-11.

22. A composition of claim 11, wherein said silicone elastomer is polysilicone-11.

23. A method of claim 19, wherein said silicone elastomer is polysilicone-11.

24. A method of claim 19, wherein:

said wax is selected from the group consisting of paraffin wax, ozokerite, candelilla wax, beeswax, and cetyl alcohol;

said non-oil emollient is selected from the group consisting of $C_{12-15}$ alkyl benzoate, neopentyl glycol dioctanoate, dibutyl adipate, and butyloctyl salicylate; and said sunscreen is selected from the group consisting of homosalate, octyl methoxycinnamte, octyl salicylate, and avobenzone;

wherein said composition is anhydrous.

25. A method of claim 25, wherein said silicone elastomer is polysilicone-11.

* * * * *